US011918457B2

(12) United States Patent
Zielke

(10) Patent No.: US 11,918,457 B2
(45) Date of Patent: Mar. 5, 2024

(54) INTRAOCULAR LENS HAVING INCREASED OPTIC DIAMETER

(71) Applicant: ALCON INC., Fribourg (CH)

(72) Inventor: Mark Andrew Zielke, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 20 days.

(21) Appl. No.: 17/123,357

(22) Filed: Dec. 16, 2020

(65) Prior Publication Data

US 2021/0177575 A1 Jun. 17, 2021

Related U.S. Application Data

(60) Provisional application No. 62/949,041, filed on Dec. 17, 2019.

(51) Int. Cl.
*A61F 2/16* (2006.01)

(52) U.S. Cl.
CPC .......... *A61F 2/1616* (2013.01); *A61F 2/1605* (2015.04); *A61F 2002/1683* (2013.01); *A61F 2002/1686* (2013.01); *A61F 2002/169* (2015.04)

(58) Field of Classification Search
CPC .. A61F 2/16; A61F 2/1616; A61F 2002/1683; A61F 2002/1686
See application file for complete search history.

(56) References Cited

U.S. PATENT DOCUMENTS

| 2005/0125056 A1* | 6/2005 | Deacon ............... A61F 2/16015 |
| | | 623/6.49 |
| 2011/0098811 A1 | 4/2011 | Hong |
| 2018/0235751 A1 | 8/2018 | Lee |
| 2019/0183632 A1 | 6/2019 | Collins et al. |
| 2019/0183636 A1 | 6/2019 | Campin et al. |

FOREIGN PATENT DOCUMENTS

| WO | 9720523 A1 | 6/1997 |
| WO | 2009143436 A2 | 11/2009 |

* cited by examiner

*Primary Examiner* — William H Matthews
(74) *Attorney, Agent, or Firm* — PATTERSON + SHERIDAN, LLP

(57) ABSTRACT

Intraocular lens (IOL) designs include having an optic with an anterior surface and a posterior surface surrounded by an optic edge. In some examples, the IOL has a plurality of haptics, each attached to the optic at a gusset, where each gusset extends beyond the optic edge toward an optic center such that the gusset at least partially overlaps with the anterior surface of the optic. In some examples, the IOL includes a ring structure integral with the optic and surrounding the perimeter of the optic edge, the ring structure having a thickness and the optic edge having a thickness, the ring structure thickness greater than the optic edge thickness.

20 Claims, 8 Drawing Sheets

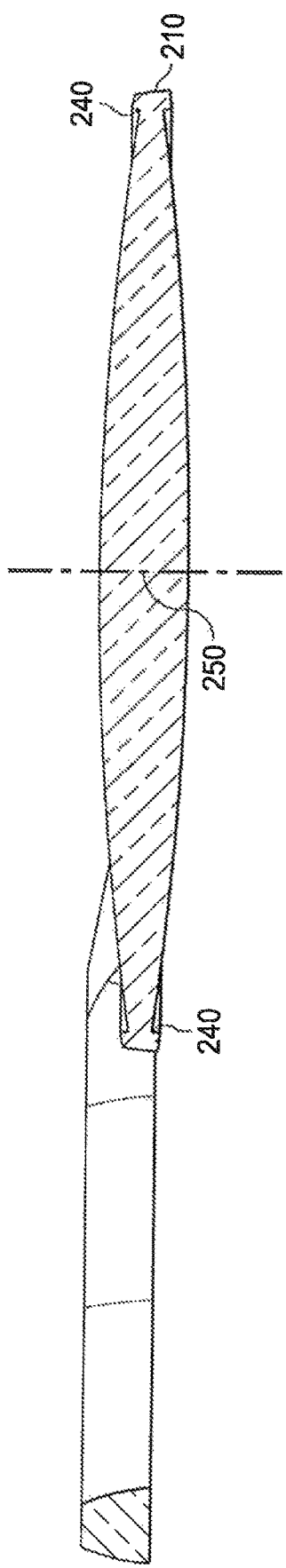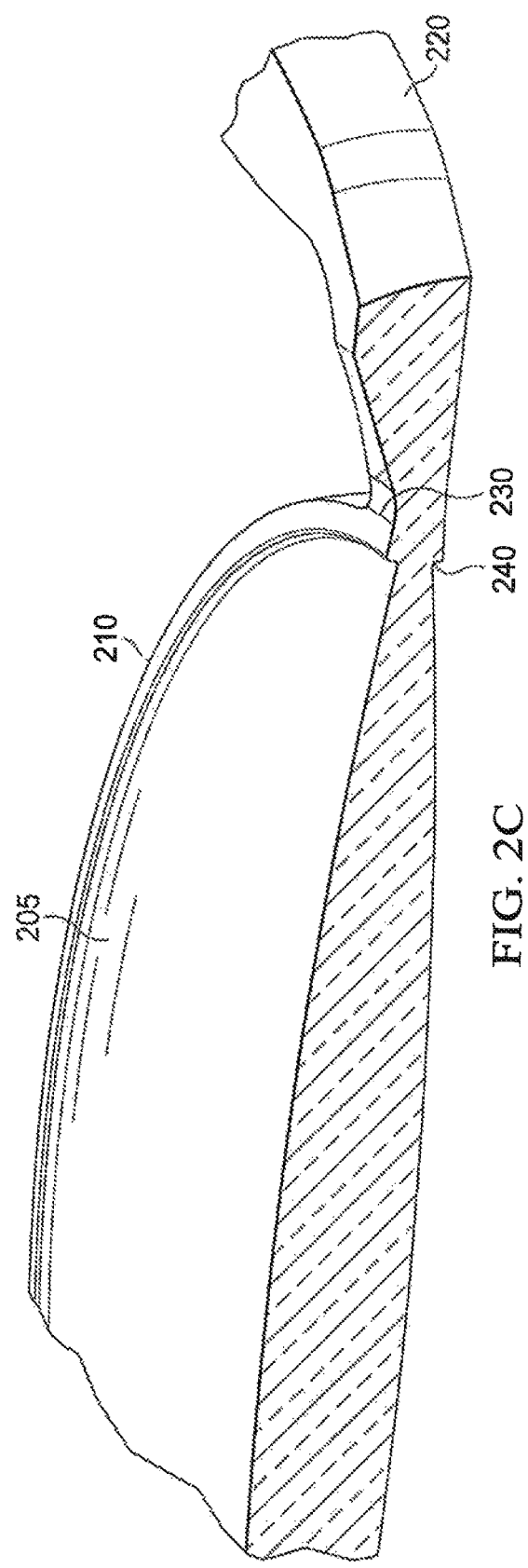

INTRAOCULAR LENS HAVING INCREASED OPTIC DIAMETER

PRIORITY CLAIM

This application claims the benefit of priority of U.S. Provisional Patent Application Ser. No. 62/949,041 titled "INTRAOCULAR LENS HAVING INCREASED OPTIC DIAMETER," filed on Dec. 17, 2019, whose inventor is Mark Andrew Zielke, which is hereby incorporated by reference in its entirety as though fully and completely set forth herein.

TECHNICAL FIELD

The present disclosure relates to intraocular lens (IOL) lens designs.

BACKGROUND

The human eye includes a cornea and a crystalline lens that are intended to focus light that enters the pupil of the eye onto the retina. However, the eye may exhibit various refractive errors, which result in light not being properly focused upon the retina, and which may reduce visual acuity. Many interventions have been developed over the years to correct various ocular aberrations. These include spectacles, contact lenses, corneal refractive surgery, such as laser-assisted in situ keratomileusis (LASIK) or corneal implants, and IOLs. IOLs are also used to treat cataracts by replacing the natural diseased crystalline lens of the eye of a patient. During typical IOL-placement surgery, an IOL is inserted into the capsular bag of a patient to replace the natural crystalline lens.

To insert an IOL into the eye, a foldable intraocular lens is inserted through the temporal clear corneal incision, often using a specially designed lens injector. The incision size is normally approximately 4 mm or less, and, with injectable IOLs, it may be approximately 3 mm or less.

The most common IOLs include an edge-to-edge optic that is approximately 6.0 mm in diameter. Visual disturbances caused by interaction of light with the edge of the optic or by light missing the edge of the optic are among problems some patients experience with a 6.0 mm lens. These visual disturbances may be reduced with a larger diameter lens, but as the diameter of an IOL increases, the volume of the IOL also increases, necessitating a larger incision. When the volume of the IOL becomes excessive, the IOL may not be insertable through a sufficiently small incision in the capsular bag.

SUMMARY

In one aspect, the present disclosure is directed to an intraocular lens, including an optic with an anterior surface and a posterior surface surrounded by an optic edge. The IOL may also include a plurality of haptics, each attached to the optic at a gusset, where each gusset extends beyond the optic edge toward an optic center such that the gusset at least partially overlaps with the anterior surface of the optic.

The IOL may include one or more of the following additional features: (i) the gusset may vary in thickness between a radially innermost edge and the haptics; (ii) the gusset may increase in thickness as it extends from a radially innermost edge away from the optic center; (iii) the gusset may have a zero thickness at a radially innermost edge and increase to a first thickness at a point radially beyond the optic edge; (iv) the gusset may have a thickness that increases monotonically as the gusset extends outwardly; (v) the optic may have a maximum thickness that is less than the thickness of the haptic; (vi) the radially innermost edge of the gusset may be at least 2.75 mm from the optic center; (vii) the optic may have a diameter between 6 mm and 8 mm, and the IOL may have a total volume between 19 mm3 and 48 mm3; (viii) the optic edge may have a thickness between 0.05 mm and 0.3 mm; (ix) the optic may have a diameter of 6 mm, and the IOL may have a total volume between 19 mm3 and 23 mm3; (x) the optic edge may have a thickness of 0.25 mm; (xi) a 21 Diopter IOL may have a total volume of 19 mm3; (xii) a 30 Diopter IOL may have a total volume of 23 mm3; (xiii) the optic may have a diameter of 7 mm, and the IOL may have a total volume between 23 mm3 and 30 mm3; (xiv) the optic edge may have a thickness of 0.1 mm; (xv) a 21 Diopter IOL may have a total volume of 23 mm3; (xvi) a 30 Diopter IOL may have a total volume of 30 mm3; xvii) the optic may have a diameter of 8 mm, and the IOL may have a total volume between 35 mm3 and 48 mm3; (xviii) the optic edge may have a thickness of 0.1 mm; (xix) a 21 Diopter IOL may have a total volume of 35 mm3; (xx) a 30 Diopter IOL may have a total volume of 48 mm3; (xxi) the optic and haptics may be made of a soft, foldable optic material; (xxii) the optic, gusset, and haptics are integrally formed to comprise a single-piece IOL.

In another aspect, an IOL comprises an optic comprising an anterior surface and a posterior surface disposed about an optical axis, the anterior surface and posterior surface surrounded by an optic edge connecting the anterior surface to the posterior surface, the optic edge defining a circumference of the optic. A gusset connects at least one haptic to at least one of the anterior surface and the posterior surface, the gusset extending from a radially innermost gusset edge to a gusset-haptic junction. The gusset at least partially overlaps with the at least one of the anterior surface and the posterior surface of the optic.

The IOL may include one or more of the following additional features: (i) the at least one of the anterior surface and the posterior surface comprises an optically active region configured to focus light to one or more focal points and a peripheral region surrounding the optically active region; and wherein the radially innermost gusset edge is in the peripheral region; (ii) the anterior surface and the posterior surface each comprise optically active regions configured to focus light to one or more focal points, each of the optically active regions extending from the center of the optic to the optic edge; (iii) the gusset protrudes from the at least one of the anterior surface and the posterior surface of the optic; (iv) the gusset protrudes from only one of the anterior surface and the posterior surface of the optic such that a cross section of the gusset is asymmetric with respect to a plane orthogonal to the optical axis; (v) the gusset increases in thickness as it extends outwardly from the innermost gusset edge; (vi) the gusset has a zero thickness at the gusset edge and increases to a maximum thickness outside the optic edge; (vii) the gusset has a thickness that increases monotonically as the gusset extends radially outwardly; (viii) a maximum thickness of the optic is less than a maximum thickness of the haptic; (ix) the radially innermost edge of the gusset is at least 2.75 mm from the optic center; (x) the optic has a diameter between 6 mm and 8 mm and the IOL has a total volume between 19 mm3 and 48 mm3; (xi) the optic edge has a thickness between 0.05 mm and 0.3 mm; (xii) the optic has a diameter of 6 mm and the IOL has a total volume between 19 mm3 and 23 mm3; (xiii)

the optic edge has a thickness of 0.25 mm; (xiv) a 21 Diopter IOL has a total volume of 19 mm3; (xv) a 30 Diopter IOL has a total volume of 23 mm3; (xvi) the optic has a diameter of 7 mm and the IOL has a total volume between 23 mm3 and 30 mm3; (xvii) the optic edge has a thickness of 0.1 mm; (xviii) a 21 Diopter IOL has a total volume of 23 mm3; (xix) a 30 Diopter IOL has a total volume of 30 mm3; (xx) the optic has a diameter of 8 mm and the IOL has a total volume between 35 mm3 and 48 mm3; (xxi) the optic edge has a thickness of 0.1 mm; (xxii) a 21 Diopter IOL has a total volume of 35 mm3; (xxiii) a 30 Diopter IOL has a total volume of 48 mm3; (xxiv) the optic, gusset, and haptics are made of a soft, foldable biocompatible material; (xxv) the optic, gusset, and haptics are integrally formed to comprise a single-piece IOL.

In another aspect, the present disclosure is directed to an IOL, including an optic having an optic edge. The IOL may also include a ring structure integral with the optic and surrounding the perimeter of the optic edge. Both the ring structure and the optic edge may have a thickness, and the ring structure thickness may be greater than the optic edge thickness. The IOL may also include a plurality of haptics attached to the ring structure.

The IOL may include one or more of the following additional features: (i) a step between the optic edge and the ring structure; (ii) the step may be angled, vertical, square, or rounded; (iii) the haptic and ring structure may attach at a haptic-ring junction that may have a thickness which may increase in thickness from the ring structure thickness to a point radially beyond the ring structure; (iv) the haptic-ring junction thickness may increase monotonically as it extends outwardly; (v) a maximum thickness of the optic may be less than the ring structure thickness; (vi) the optic, ring structure, and haptics may be made of a soft, foldable optic material; (vii) the optic may have a diameter between 6 mm and 8 mm, and the IOL may have a total volume between 14 mm3 and 48 mm3; (viii) the optic may have a diameter of 6 mm, and the IOL may have a total volume between 14 mm3 and 18 mm3; (ix) the optic may have a diameter of 7 mm, and the IOL may have a total volume between 23 mm3 and 30 mm3; (x) the optic may have a diameter of 8 mm, and the IOL may have a total volume between 35 mm3 and 48 mm3; (xi) the optic edge thickness may be between 0.05 mm and 0.3 mm; (xii) the optic edge thickness may be 0.15 mm; viii) the ring structure thickness may be between 0.2 mm and 0.5 mm; (xiv) the optic may be made of a first material, and the ring structure and haptics may be made of a second material. The second material may have a higher stiffness than the first material; (xv) the first material may be a soft, foldable optic material; (xvi) the first material may be Acrysof, p-hydroxyethyl methacrylate, a hydrophobic silicon polymer, acrylates, or hydrophilic 2-HEMA homopolymers; xvii) the second material may be Poly(methyl methacrylate) (p-MMA), polyvinylidene fluoride (PVDF), polysulfones, or an acrylic; (xviii) the ring structure and the haptics may be molded or bonded to the optic edge; (xix) the optic may have a diameter between 6 mm and 8 mm, and the IOL may have a total volume between 13 mm3 and 46 mm3; (xx) the optic may have a diameter of 6 mm, and the IOL may have a total volume between 13 mm3 and 17 mm3; (xxi) the optic may have a diameter of 7 mm, and the IOL may have a total volume between 21 mm3 and 28 mm3; (xxii) the optic may have a diameter of 8 mm, and the IOL may have a total volume between 34 mm3 and 46 mm3.

BRIEF DESCRIPTION OF THE DRAWINGS

For a more complete understanding of the present disclosure, reference is now made to the following description, taken in conjunction with the accompanying drawings illustrating aspects of the present disclosure, in which like components have like numerals, including with alphabetic designations of variants, such as 10a, 10b, and in which:

FIG. 2B is a cross-section view of an IOL having a ring structure around the perimeter of the optic edge.

FIG. 2C is a perspective cross-section view of an IOL having a ring structure around the perimeter of the optic edge.

DETAILED DESCRIPTION

Figure 1A:
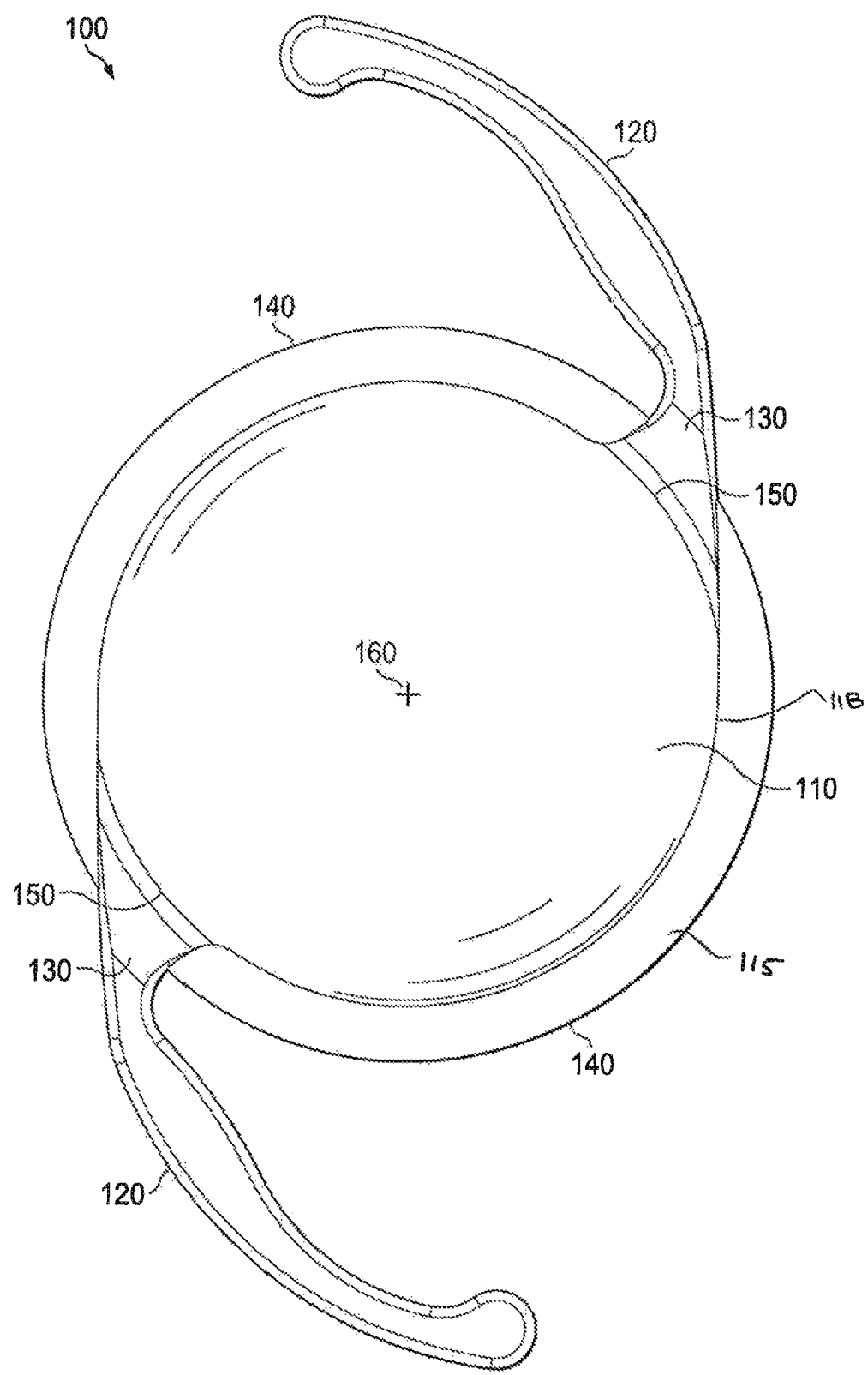
FIG. 1A is a top view of the anterior surface of an IOL, where the gusset extends beyond the optic edge toward an optic center, partially overlapping with the anterior surface of the optic.
Figure 1B:
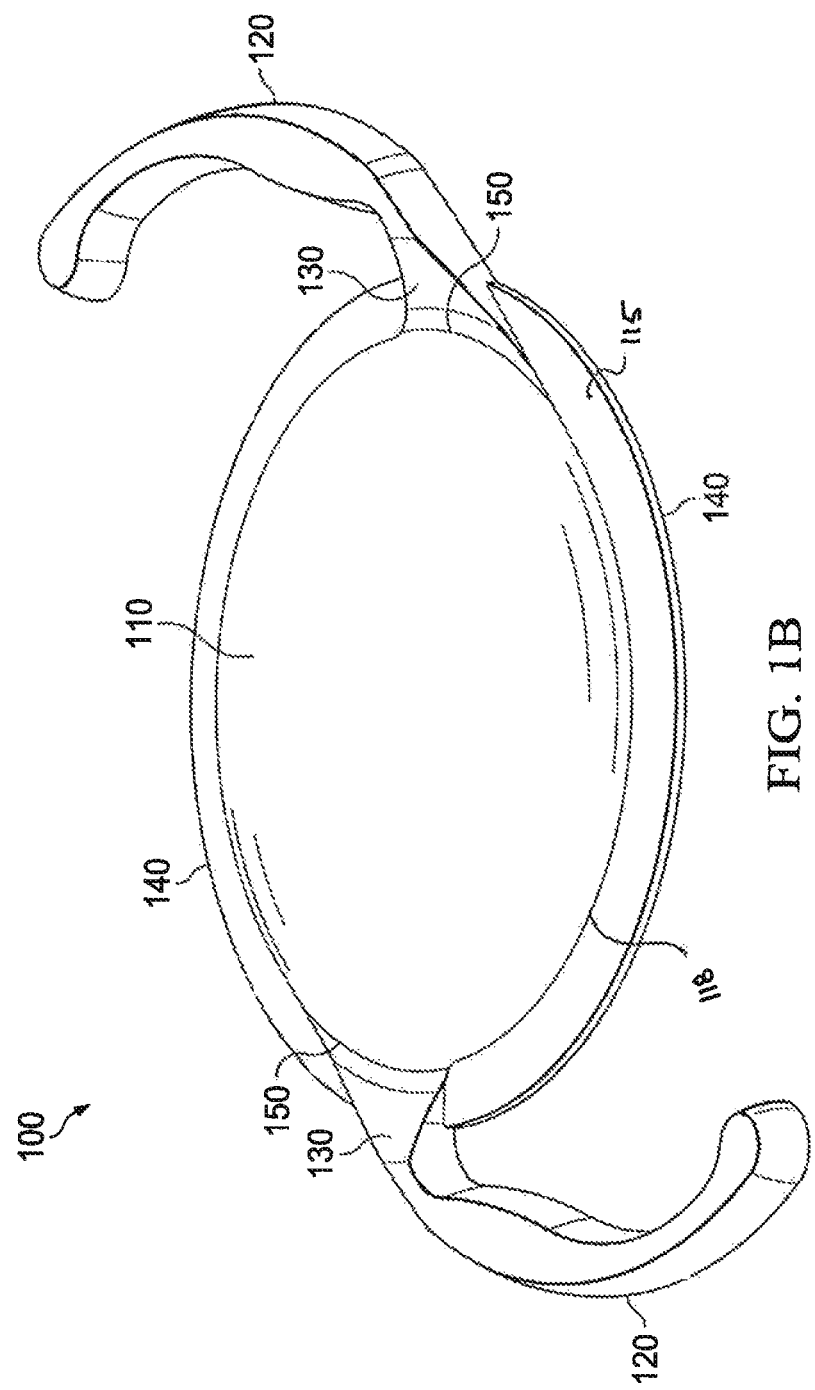
FIG. 1B is a perspective view of an IOL, where the gusset extends beyond the optic edge toward an optic center, partially overlapping with the anterior surface of the optic.
Figure 1C:
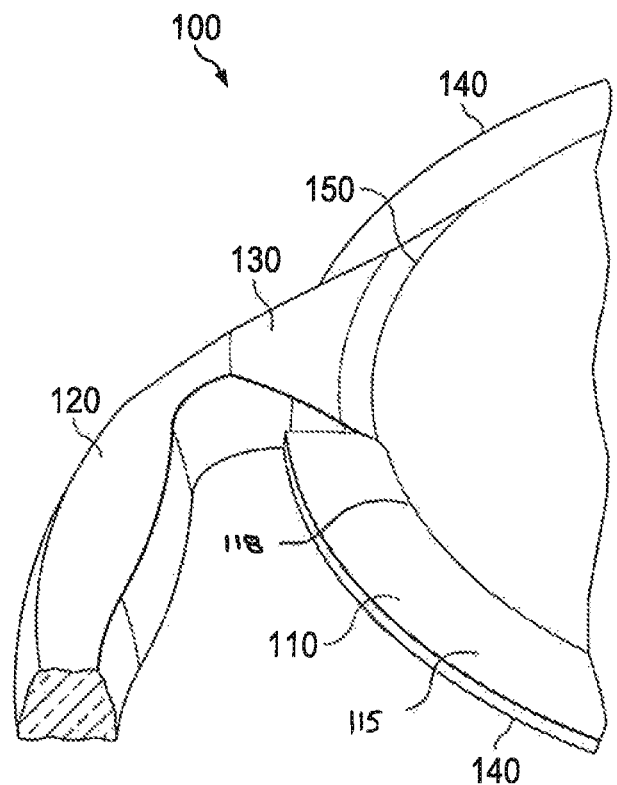
FIG. 1C is an enlarged view of a gusset of an IOL, where the gusset extends beyond the optic edge toward an optic center, partially overlapping with the anterior surface of the optic.
Figure 1D:
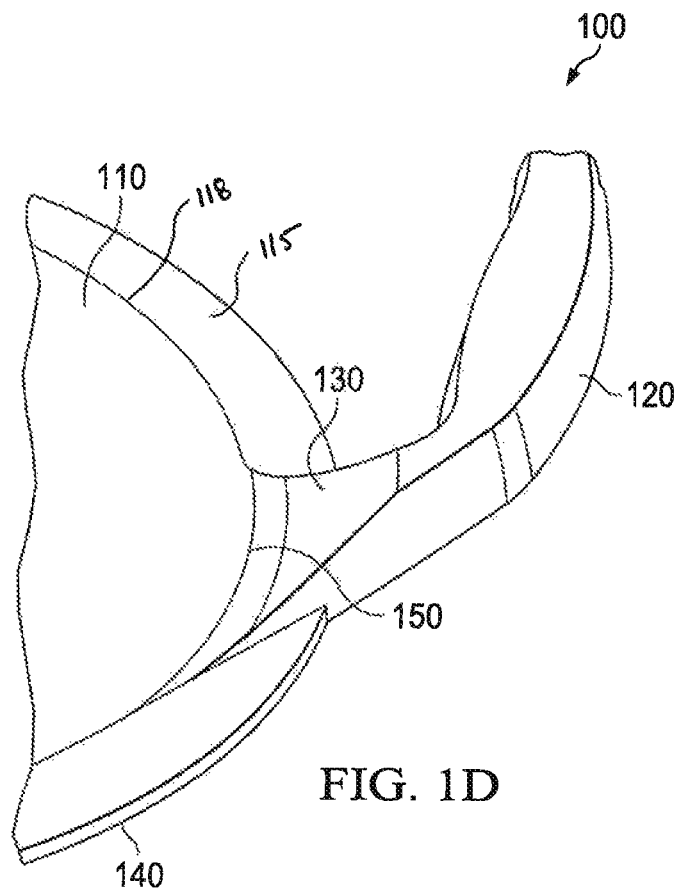
FIG. 1D is an enlarged view of a gusset of an IOL, where the gusset extends beyond the optic edge toward an optic center, partially overlapping with the anterior surface of the optic.

The present disclosure relates to an IOL, where the diameter of the IOL is increased without significantly increasing the overall volume. This may be achieved by using gussets to connect the optic to the haptic. Each gusset may originate on the anterior or posterior surface of the optic itself (rather than at the optic edge) and extend radially outwardly toward the haptic, thus partially overlapping with the anterior (or posterior) surface of the optic. The gusset may be located outside an optically active area of the optic (e.g., beyond 2.5-3 mm from the optic center) to minimize the possibility of an adverse impact on a patient's vision. Alternatively, the entire posterior and/or anterior surfaces of the optic may be optically active. (An optically active area of the IOL may include one or more surface profiles on the anterior and/or posterior surfaces of the optic which are collectively configured to focus light at one or more focal points to provide vision correction for a patient.) By coupling the haptics with a gusset connected on the anterior or posterior surface of the optic, the optic edge is not required to support the haptic structurally. Accordingly, the optic can be made thinner, reducing overall volume even with relatively large optics (e.g., having a diameter greater than 6 mm).

Such benefits may alternatively or, when appropriate, additionally be achieved by using a ring structure around the perimeter of the optic edge, where the ring structure may be made of the same material as the optic or may be made of a second material having a higher stiffness than a first material of which the optic is made.

In FIGS. 1A-D, the anterior surface of an IOL 100 is shown having an optic 110 and two haptics 120 attached to optic 110 by gussets 130.

Optic 110 has an anterior surface and a posterior surface (not shown) that are connected and surrounded by an optic edge 140. By decreasing the thickness of optic 110 at and approaching optic edge 140, the overall volume of IOL 100 may be decreased (thickness being measured anteriorly-to-posteriorly along the optical axis (OA)). For example, the thickness of optic 110 at its centermost point, optic center 160 (the point of maximum thickness for a biconvex lens), may be between 0.2 mm and 2 mm, while optic edge 140 may have a thickness between 0.05 mm and 0.3 mm. The thickness of optic 110 may vary based on the materials used for optic 110. For example, a stiffer material may have an optic edge 140 having a thickness of between 0.05 mm and 0.1 mm, while a softer material may have an optic edge 140 having a thickness of between 0.1 mm and 0.3 mm. The maximum thickness of optic 110 may be less than the thickness of haptics 120 (thickness being measured along the optical axis of the optic).

One or more haptics 120 connect optic 110 to a capsular bag to hold optic 110 in a stable position within the capsular bag. The embodiment shown in FIGS. 1A-D shows an IOL having two, open-loop haptics, but the number and shape of the haptics may vary. The number of haptics may include, but are not limited to, one, two, three, four, five, or six. The shape of the haptics may include, but are not limited to, plate, open-loop, such as C-Loop or J-Loop, angular, planar, or off-set haptics. The overall length of IOL 100, including haptics, may be between 10 mm and 15 mm. The thickest portion of haptics 120 (thickness being measured along an axis parallel to the optical axis of the lens) may be between 0.2 mm and 1 mm. For example, the thickest part of haptics 120 may be 0.6 mm.

The gussets 130 (shown in more detail in FIGS. 1C and 1D) attach optic 110 to the two haptics 120. Each gusset 130 extends radially inward from the haptic 120, across optic edge 140, and toward optic center 160, such that gusset 130 at least partially overlaps with and extends onto the anterior surface of the optic 110. Gussets 130 each have a radially innermost edge 150 located on the anterior surface of IOL 100 radially inwardly from where optic edge 140 would be if the gussets 130 were not present. Radially innermost edge 150 of gusset 130 may be between 2.5 mm and 3 mm in a radially outward direction from optic center 160 to prevent obstruction of a patient's vision. For example, radially innermost edge 150 of gusset 130 may be 2.75 mm radially outwardly from optic center 160 in some embodiments, such that the distance across the optic from one gusset edge 150 to the other is 5.5 mm. Radially innermost edge 150 of gusset 130 may be between 0.1 and 1.5 mm in a radially inwardly direction from a distance corresponding to optic edge 140 (i.e., where optic edge 140 would be if not for the presence of gusset 130). For example, radially innermost edge 150 of gusset 130 may be 1.25 mm radially inward from optic edge 140.

In some examples, an optical surface profile defining an optically active area of the anterior and/or posterior surface of optic 110 (e.g., a spherical or aspheric monofocal, multifocal, or extended depth of focus surface profile) may extend continuously from optic center 160 to optic edge 140 (excepting areas where gussets 130 impinge). In other examples, the optical surface profile defining an optically active area of the anterior and/or posterior surface may extend radially from optic center 160 a distance between optic center 160 and optic edge 140, e.g., about 2.5 to 3 mm radially from optic center 160. In such examples, a peripheral area 115 of the anterior surface outside the optical surface profile may have a different surface profile than the central area of optic 110. For example, a profile of such a peripheral area 115 may be flat or may have a thickness which varies differently than the optic surface profile. In examples which include a peripheral area 115, the peripheral area 115 may be separated from the optically active area at a boundary 118, which may be visibly perceptible or not. In examples which do not include a peripheral area 115, boundary 118 is not present.

Gusset 130 may vary in thickness between radially innermost edge 150 and haptics 120. Radially innermost edge 150 may be level or flush with optic 110 at radially innermost edge 150, having zero thickness. As gusset 130 extends from radially innermost edge 150 radially outwardly away from optic center 160, the thickness of gusset 130 may increase monotonically. The thickness may continue to increase to a first peak thickness 135 located at a point radially outward from optic edge 140.

In conventional IOLs, haptics are connected to an optic at a haptic-optic junction along a perimeter of the optic edge. This design necessitates a threshold edge thickness for the stability of this connection. Due to the required edge thickness, extending the optic to larger diameters (e.g., beyond 6 mm) increases volume to a degree that makes small-incision delivery (e.g., 2-3 mm incisions or smaller) difficult or impossible.

In the disclosed design, however, that gusset 130 connecting optic 110 and haptic 120 at least partially overlaps with the anterior and/or posterior surface of optic 110, thus using part of the anterior surface for a haptic-optic connection rather than only the perimeter of the optic edge. Accordingly, gusset 130 may protrude from the anterior and/or posterior surface of the optic. In some examples, gusset 130 protrudes from only one of the anterior or posterior surface, and is flush on the opposite surface.

As a result, the diameter of optic 110 may be increased relative to a conventional optic, while corresponding increases in volume are minimized so that the IOL may still be inserted through a small incision. In various examples, the volume of optic 110 may be between 10 mm3 and 40 mm3.

Optic 110 may have a diameter in the range of 6 to 8 mm. In some embodiments, the diameter of optic 110 may be 6 mm, 7 mm, or 8 mm, and the total volume of the IOL may be between approximately 19 mm3 and 48 mm3. The thickness of optic edge 140 may range between approximately 0.05 mm3 and 0.3 mm3.

In a 6 mm optic diameter embodiment, optic edge 140 may have a thickness of 0.25 mm. In this embodiment, IOL 100 may have a total volume between 19 mm3 and 23 mm3. For example, a 21 diopter IOL may have a total IOL volume of 19 mm3, and a 30 diopter IOL may have a total IOL volume of 23 mm3.

In a 7 mm optic diameter embodiment, optic edge 140 may have a thickness of 0.1 mm. In this embodiment, IOL 100 may have a total volume between 23 mm3 and 30 mm3. For example, a 21 diopter IOL may have a total IOL volume of 23 mm3, and a 30 diopter IOL may have a total IOL volume of 30 mm3.

In an 8 mm optic diameter embodiment, optic edge 140 may have a thickness of 0.1 mm. In this embodiment, IOL 100 may have a total volume between 35 mm3 and 48 mm3.

For example, a 21 diopter IOL may have a total IOL volume of 35 mm3, and a 30 diopter IOL may have a total IOL volume of 48 mm3.

IOL 100 may be inserted through an incision of between 1 mm and 3 mm. It is important to maintain a small incision because too large of an incision may lead to a flattening effect of the cornea. Furthermore, a smaller incision may be better able to seal after surgery to prevent leakage and tear film contamination. Quicker sealing of the incision may help prevent or reduce the risk of developing surgically induced astigmatism or endophthalmitis. Because fluid flow is related to the size of the phaco needle, using sub-1 mm incisions reduces the flow rate and makes surgery significantly slower. Incisions more than 3 mm tend to have a greater flattening effect on the cornea at that meridian. In addition, the incision should be small enough to seal effectively after the surgery to prevent leakage as well as tear film influx, which could increase the risk of endophthalmitis. So, the ideal incision size for cataract surgery is between 1 mm and 3 mm, which is small enough to reduce astigmatic effect from the incision and the risk of infection due to leakage or tear film contamination.

Optic 110, haptics 120, and gussets 130 may be made of a soft, foldable optic material, or of any material suitable to be a lens, while also providing sufficient mechanical support. For example, the material may be hydrogel, acrylate, or silicon-based material, as known in the field of ophthalmology.

Figure 2A:
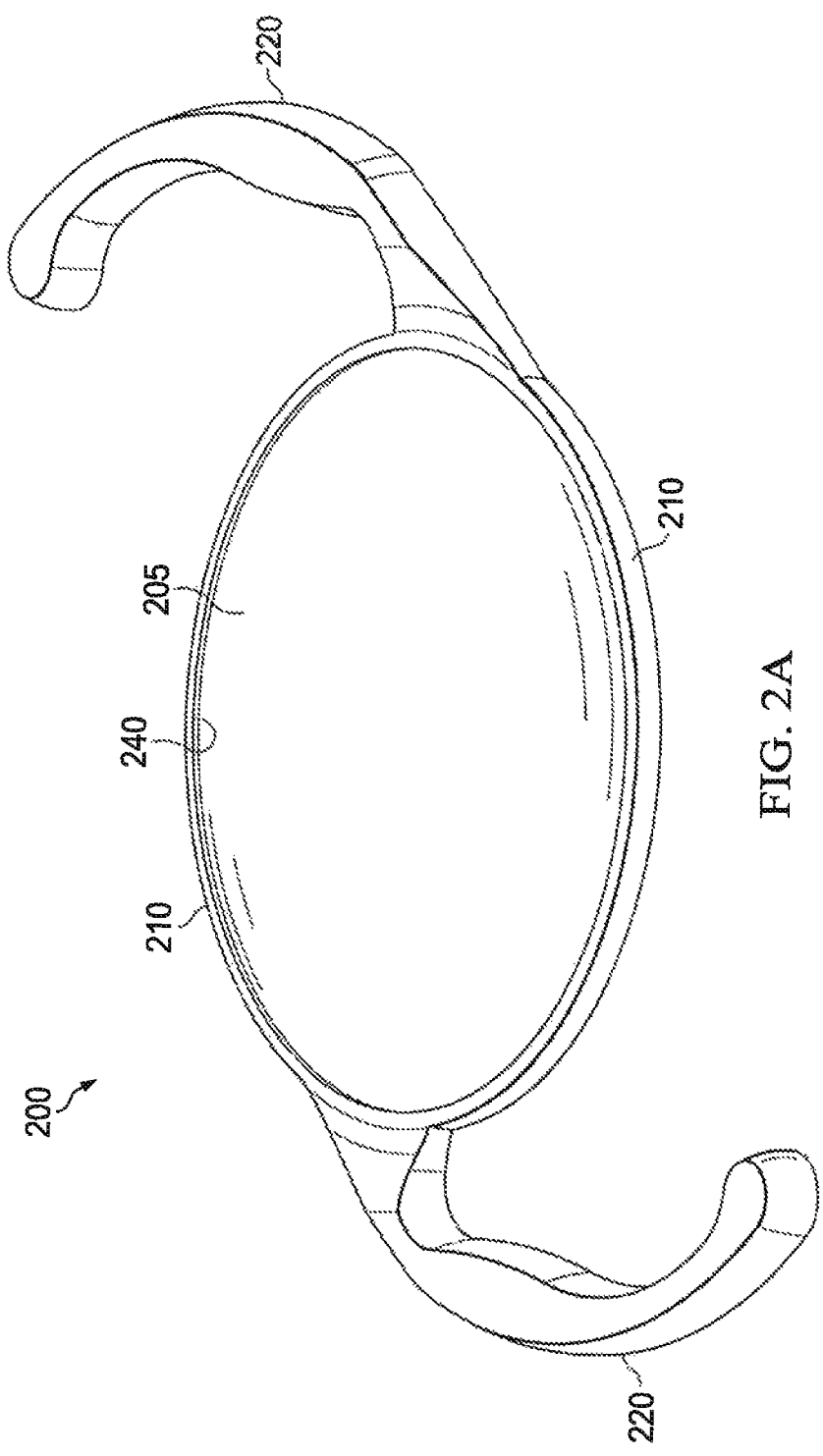
FIG. 2A is a perspective view of an IOL having a ring structure around the perimeter of the optic edge.

In another embodiment, as shown in FIGS. 2A-C, the present disclosure relates to an IOL 200 having a ring structure 210 integral with the optic 205 and surrounding the perimeter of the optic edge 240. Adding the stiff, outer ring structure 210 allows for a thinner optic 205, which reduces the overall volume of the IOL 200. The optic 205 may be thinner because the ring structure 210 provides a base and mechanical support for the haptics 220 in lieu of the optic 205 providing the base and mechanical support.

In FIG. 2A, IOL 200 is shown having a ring structure 210 around the perimeter of optic edge 240. The ring structure 210 may be thicker than the optic edge 240 and may be between 0.2 mm and 0.5 mm. For example, the thickness of the ring structure 210 may be 0.3 mm.

Between the optic edge and ring structure, IOL 200 may include a step. The shape of the step 200 may be, must is not limited to, angled, vertical, square, or round.

A plurality of haptics 220 may attach to the ring structure 210 at opposite sides at a haptic-ring junction. At the point of connection 230 (shown in FIG. 2C), the haptic-ring junction may by the same thickness as the ring structure 210, and then may increase in thickness from the ring structure thickness to a point radially beyond the ring structure. The haptic-ring junction thickness may increase monotonically as it extends outwardly. The embodiment shown in FIG. 2A shows an IOL having two, open-loop haptics, but the number and shape of the haptics may vary. The number of haptics may include, but are not limited to, two, three, four, five, or six. The shape of the haptics may include, but are not limited to, plate, open-loop, such as C-Loop or J-Loop, angular, planar, or off-set haptics.

FIGS. 2B-C show cross sections of IOL 200. In embodiments, the thickness of optic edge 240 may be between 0.05 mm and 0.3 mm. For example, the thickness of optic edge 240 may be 0.15 mm. The maximum thickness of optic 205 at its center 250 may be less than the ring structure thickness. The thickness of optic 205 at its center 250 depends on the IOL power, material refractive index, and other IOL geometry. In embodiments, the thickness of optic 205 at its center 250 may be between 0.2 mm and 2 mm.

Reducing the overall lens thickness allows for a larger optic diameter without increasing the volume. So, optic 205 may have a larger diameter than a conventional optic, while maintaining an acceptable volume that may still insert through a small incision. Ring structure 210 having a thinner optic 205 provides for an IOL 200 with a volume that may fit through a small incision. For example, IOL 200 may be inserted through an incision of between 1 mm and 3 mm. The diameter of the optic 205 may be between 6 mm and 8 mm. In some embodiments, the diameter of the optic may be 6 mm, 7 mm, or 8 mm, and the total volume of IOL 200 may be between approximately 14 mm3 and 48 mm3.

In a 6 mm optic diameter embodiment, optic edge 240 may have a thickness of 0.1 mm. In this embodiment, IOL 200 may have a total volume between 14 mm3 and 18 mm3. For example, a 21 diopter IOL may have a total IOL volume of 14 mm3, and a 30 diopter IOL may have a total IOL volume of 18 mm3.

In a 7 mm optic diameter embodiment, optic edge 240 may have a thickness of 0.1 mm. In this embodiment, IOL 200 may have a total volume between 23 mm3 and 30 mm3. For example, a 21 diopter IOL may have a total IOL volume of 23 mm3, and a 30 diopter IOL may have a total IOL volume of 30 mm3.

In an 8 mm optic diameter embodiment, optic edge 240 may have a thickness of 0.1 mm. In this embodiment, IOL 200 may have a total volume between 35 mm3 and 48 mm3. For example, a 21 diopter IOL may have a total IOL volume of 35 mm3, and a 30 diopter IOL may have a total IOL volume of 48 mm3.

Optic 205, ring structure 210, and haptics 220 may be the same material. Using the same material for the entire IOL 200 allows the entire IOL 200 to be formed together. This may eliminate a need for bonding or overmolding of the components. The material used for optic 205, ring structure 210, and haptics 220 may be a soft, foldable optic material. The softer material may have a modulus of 6 MPa or lower at 35° C. For example, the material may be hydrogel, acrylate, or silicon-based material, as known in the field of ophthalmology.

Figure 3A:
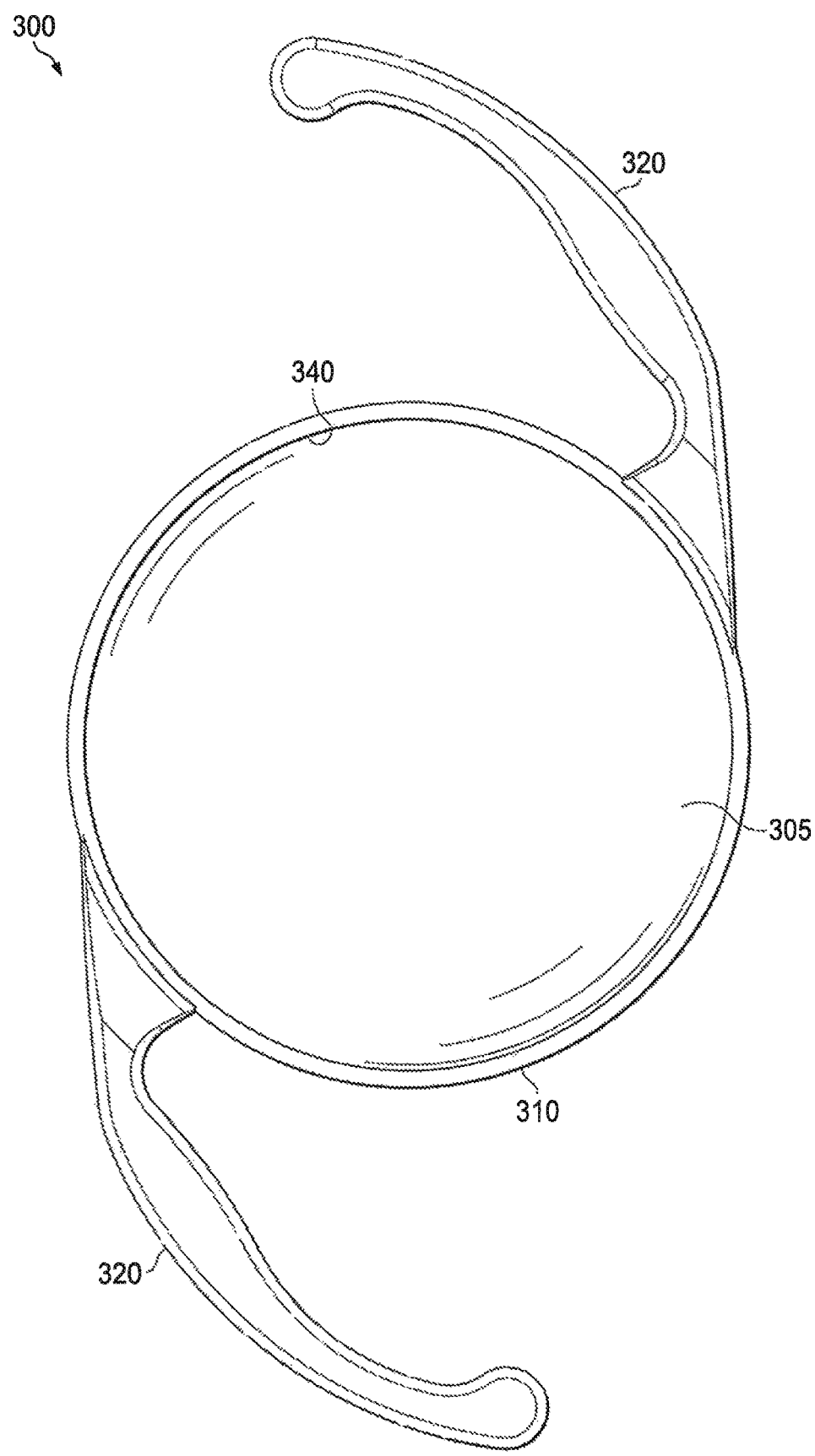
FIG. 3A is a top view of an IOL having a ring structure around the perimeter of the optic edge, where the optic is a different material than the ring structure and haptics.
Figure 3B:
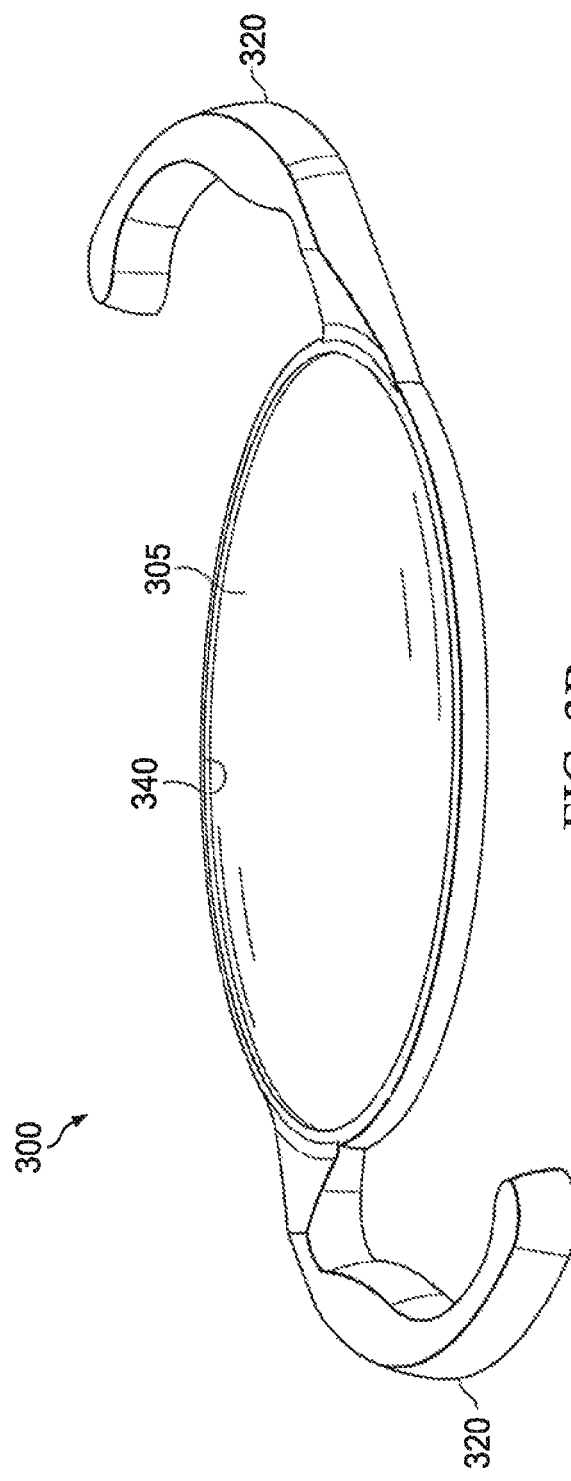
FIG. 3B is a perspective view of an IOL having a ring structure around the perimeter of the optic edge, where the optic is a different material than the ring structure and haptics.
Figure 3C:
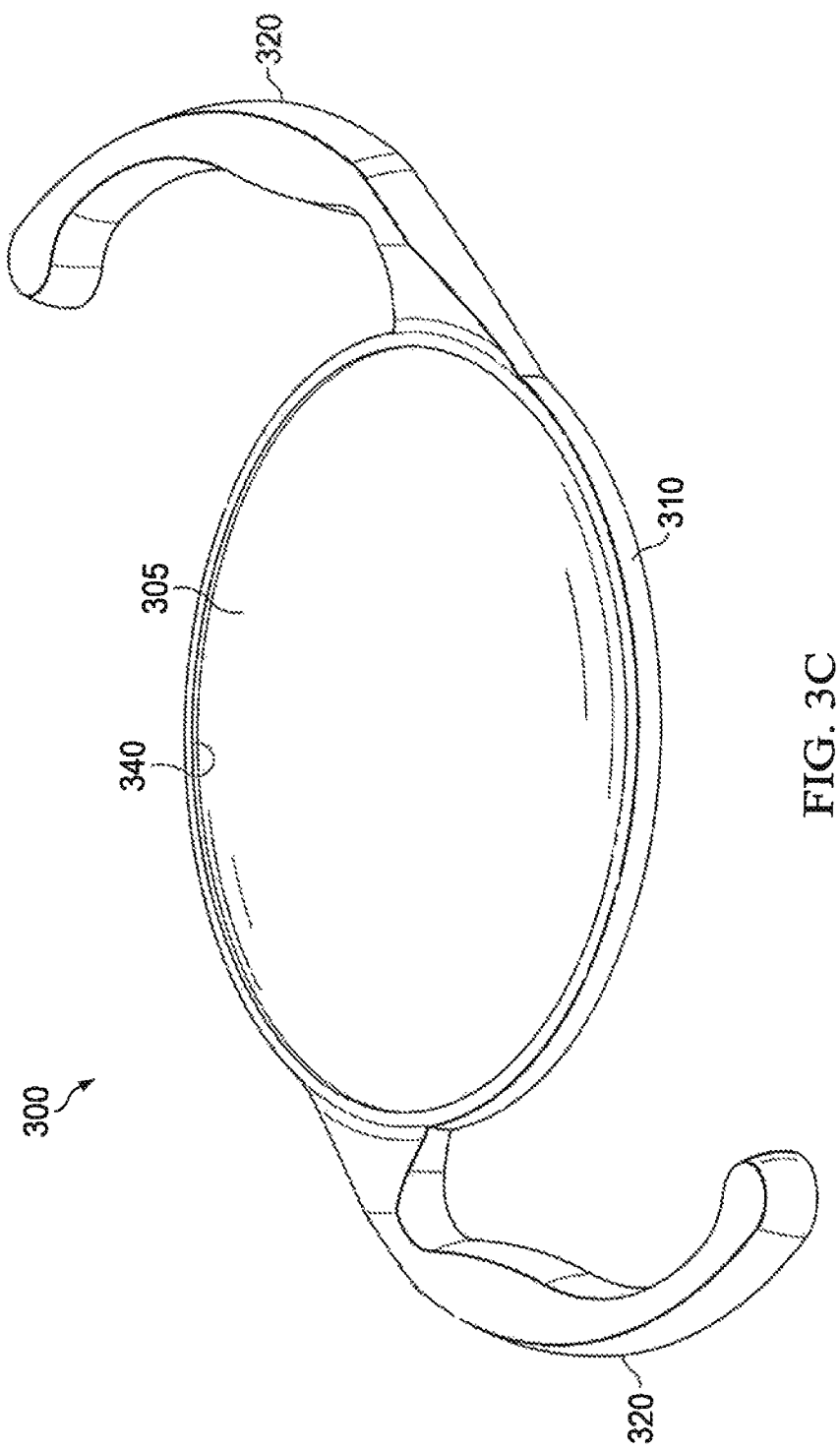
FIG. 3C is a perspective view of an IOL having a ring structure around the perimeter of the optic edge, where the optic is a different material than the ring structure and haptics.

In another embodiment, as shown in FIGS. 3A-C, the present disclosure relates to an IOL 300 having a ring structure 310 around the perimeter of the optic edge 340, where the optic 305 is a different material than ring structure 310 and haptics 320. For example, optic 305 may be made of a first material, and ring structure 310 and haptics 320 may be made of a second material. The stiffness of ring structure 310 may provide support for the softer optic 305. Optic 305 and ring structure 310 may be attached via bonding or overmolding. Bonding or overmolding are processes where a single part is created using two or more different materials in combination. For example, first an optic 305 may be molded. Then ring structure 310 and haptics 320 may be molded onto or around optic 305.

Optic 305 may be made of a first material. For example, it may be made of a soft, foldable optic material. By way of example, optic 305 may be made of Acrysof, p-hydroxyethyl methacrylate, a hydrophobic silicon polymer, acrylates, or hydrophilic 2-HEMA homopolymers. In embodiments, optic 305 may be made of a soft acrylate.

Ring structure 310 and haptics 320 may be made of a second material. For example, ring structure 310 and haptics 320 may be made of a stiffer material than optic 305, removing the need for a thicker optic edge 340. Using a stiffer material for ring structure 310 and haptics 320 can lower the overall IOL 300 volume to help with small delivery incision and allow IOL 300 to be inserted through an incision of between 1 mm and 3 mm. Ring structure 310 and haptic 320 materials may have suitable strength and stiffness characteristics to provide stability in a capsular bag while remaining foldable, allowing for delivery through a small incision in the capsular bag. A stiffer material resists deformation in response to an applied force, as compared to a more flexible material. The stiffer material may have a modulus at least 30% higher than the modulus of the softer material. In embodiments, the stiffer material may have a modulus of 7.8 MPa or higher at 35° C. Ring structure 310 and haptics 320 may be made of a second material, such as a stiff haptic material, including, for example, Poly(methyl methacrylate) (p-MMA), polyvinylidene fluoride (PVDF), polysulfones, an acrylic, or of any material having a suitable stiffness to support the optic 305, while still being foldable.

In embodiments, ring structure 310 and optic edge 340 may be the same thickness. The thickness of ring structure 310 and optic edge 340 may be between 0.05 mm and 0.25 mm. For example, ring structure 310 and optic edge 340 may be 0.15 mm.

In other embodiments, ring structure 310 may be thicker than optic edge 340. The thickness of ring structure 310 may be between 0.1 mm and 0.5 mm. For example, the thickness of ring structure 310 may be 0.15 mm. The thickness of optic edge 340 may be between 0.05 mm and 0.3 mm. The ring structure 310 may be between 30% and 500% times thicker than the optic edge 340.

The diameter of optic 305 may be 6 mm to 8 mm. In some embodiments, the diameter of optic 305 may be 6 mm, 7 mm, or 8 mm, and the total volume of IOL 300 may be between 13 mm3 and 46 mm3.

In a 6 mm optic diameter embodiment, optic edge 340 may have a thickness of 0.1 mm. In this embodiment, IOL 300 may have a total volume between 13 mm3 and 17 mm3. For example, a 21 diopter IOL may have a total IOL volume of 13 mm3, and a 30 diopter IOL may have a total IOL volume of 17 mm3.

In a 7 mm optic diameter embodiment, optic edge 340 may have a thickness of 0.1 mm. In this embodiment, IOL 300 may have a total volume between 21 mm3 and 28 mm3. For example, a 21 diopter IOL may have a total IOL volume of 21 mm3, and a 30 diopter IOL may have a total IOL volume of 28 mm3.

In an 8 mm optic diameter embodiment, optic edge 340 may have a thickness of 0.1 mm. In this embodiment, IOL 300 may have a total volume between 34 mm3 and 46 mm3. For example, a 21 diopter IOL may have a total IOL volume of 34 mm3, and a 30 diopter IOL may have a total IOL volume of 46 mm3.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL), comprising:
   an optic comprising an anterior surface and a posterior surface, a circumference of the optic surrounded by an optic edge; and
   a plurality of haptics, each attached to the optic at a gusset, wherein:
   each gusset extends beyond the optic edge toward an optic center such that the gusset at least partially overlaps with the anterior surface of the optic,
   each gusset is spaced apart along the optic edge and overlaps with only a portion of the circumference of the optic edge, and
   each gusset protrudes from only one of the anterior surface or the posterior surface of the optic, and is flush with a surface opposite the anterior surface or the posterior surface, such that a cross section of the gusset is asymmetric with respect to a plane orthogonal to an optical axis of the optic.

2. The IOL of claim 1, wherein the gusset varies in thickness between a radially innermost edge and the haptics.

3. The IOL of claim 1, wherein the gusset increases in thickness as it extends from a radially innermost edge away from the optic center.

4. The IOL of claim 1, wherein a radially innermost edge of the gusset is at least 2.75 mm (millimeters) from the optic center.

5. The IOL of claim 1, wherein the optic has a diameter between 6 mm and 8 mm and the IOL has a total volume between 19 mm$^3$ (cubic millimeters) and 48 mm$^3$.

6. The IOL of claim 1, wherein the optic edge has a thickness between 0.05 mm and 0.3 mm.

7. The IOL of claim 1, wherein the optic has a diameter of 7 mm and the IOL has a total volume between 23 mm$^3$ and 30 mm$^3$.

8. The IOL of claim 1, wherein the optic has a diameter of 8 mm and the IOL has a total volume between 35 mm$^3$ and 48 mm$^3$.

9. An intraocular lens (IOL), comprising:
   an optic comprising an anterior surface and a posterior surface disposed about an optical axis, the anterior surface and posterior surface surrounded by an optic edge connecting the anterior surface to the posterior surface, a circumference of the optic surrounded by the optic edge; and
   a gusset connecting at least one haptic to at least one of the anterior surface and the posterior surface, the gusset extending from a radially innermost gusset edge to a gusset-haptic junction;
   wherein the gusset at least partially overlaps with the at least one of the anterior surface and the posterior surface of the optic,
   wherein the gusset overlaps with only a portion of the circumference of the optic edge, and
   wherein the gusset protrudes from only one of the anterior surface or the posterior surface of the optic, and is flush with a surface opposite the anterior surface or the posterior surface, such that a cross section of the gusset is asymmetric with respect to a plane orthogonal to the optical axis.

10. The IOL of claim 9, wherein the at least one of the anterior surface and the posterior surface comprises an optically active region configured to focus light to one or more focal points and a peripheral region surrounding the optically active region; and wherein the radially innermost gusset edge is in the peripheral region.

11. The IOL of claim 9, wherein the radially innermost gusset edge of the gusset is at least 2.75 mm (millimeters) from an optic center.

12. The IOL of claim 9, wherein the optic has a diameter between 6 mm and 8 mm and the IOL has a total volume between 19 mm$^3$ (cubic millimeters) and 48 mm$^3$.

13. An intraocular lens (IOL), comprising:

an optic comprising an anterior surface and a posterior surface disposed about an optical axis, the anterior surface and posterior surface surrounded by an optic edge connecting the anterior surface to the posterior surface, a ring structure integral with the optic and surrounding a circumference of the optic edge, the ring structure extending outward from the anterior surface and the posterior surface along an axis parallel to the optical axis at a connection point of the ring structure and the optic edge, the ring structure having a first thickness and the optic edge having a second thickness, wherein first thickness is greater than the second thickness; and a plurality of haptics attached to the ring structure, wherein:

at least one haptic of the plurality of haptics and the ring structure attach at a haptic-ring junction, the haptic-ring junction is disposed radially outward from the optic edge, the haptic-ring junction has a third thickness, and the third thickness increases from the first thickness to a point radially beyond the ring structure.

14. The IOL of claim 13, further comprising a step between the optic edge and the ring structure.

15. The IOL of claim 13, wherein the optic has a diameter between 6 mm and 8 mm and the IOL has a total volume between 14 mm$^3$ (cubic millimeters) and 48 mm$^3$.

16. The IOL of claim 13, wherein the first thickness is between 0.2 mm (millimeters) and 0.5 mm.

17. The IOL of claim 13, wherein the optic is made of a first material, and the ring structure and haptics are made of a second material, the second material having a higher stiffness than the first material.

18. The IOL of claim 13, wherein the ring structure and the haptics are molded or bonded to the optic edge.

19. The IOL of claim 1, wherein a peripheral area of the anterior surface of the optic has a different surface profile than a central area of the anterior surface of the optic.

20. The IOL of claim 13, wherein the ring structure is coupled to the optic only at a circumferential perimeter of the optic edge.

* * * * *